United States Patent
Guo et al.

(10) Patent No.: US 6,623,754 B2
(45) Date of Patent: Sep. 23, 2003

(54) DOSAGE FORM OF N-ACETYL CYSTEINE

(75) Inventors: Jian-Hwa Guo, Hudson, OH (US); William Robert Wilber, Avon Lake, OH (US)

(73) Assignee: Noveon IP Holdings Corp., Cleveland, OH (US)

( * ) Notice: Subject to any disclaimer, the term of this patent is extended or adjusted under 35 U.S.C. 154(b) by 0 days.

(21) Appl. No.: 09/681,689

(22) Filed: May 21, 2001

(65) Prior Publication Data

US 2003/0003148 A1 Jan. 2, 2003

(51) Int. Cl.[7] .................................................. A61K 9/20
(52) U.S. Cl. ........................ 424/464; 424/465; 424/468
(58) Field of Search .................. 424/464, 400, 424/465, 405, 468, 470

(56) References Cited

U.S. PATENT DOCUMENTS

| | | | |
|---|---|---|---|
| 2,798,053 A | | 7/1957 | Brown .................... 260/2.2 |
| 3,915,921 A | * | 10/1975 | Schlatzer, Jr. ............. 260/17.4 |
| 4,267,103 A | * | 5/1981 | Cohen ..................... 260/17.4 |
| 4,968,506 A | * | 11/1990 | Appelgren et al. ......... 424/456 |
| 4,996,047 A | * | 2/1991 | Kehelleher et al. ......... 424/79 |
| 5,145,644 A | * | 9/1992 | Park et al. ................ 422/28 |
| 5,288,814 A | | 2/1994 | Long, II et al. ........... 525/450 |
| 5,349,030 A | | 9/1994 | Long, II et al. ........... 525/450 |
| 5,716,991 A | | 2/1998 | Jones ..................... 514/562 |
| 5,753,656 A | * | 5/1998 | Sakai et al. ............... 514/249 |
| 5,766,623 A | | 6/1998 | Ayres et al. .............. 424/441 |
| 5,852,055 A | | 12/1998 | Jones ..................... 514/562 |
| 6,060,486 A | * | 5/2000 | Urashima et al. .......... 514/319 |

FOREIGN PATENT DOCUMENTS

| | | | |
|---|---|---|---|
| WO | WO0006151 | 2/2000 | |
| WO | WO0008092 | 2/2000 | |
| WO | WO 00/08092 | * 2/2000 | .............. C08J/3/12 |
| WO | WO0137808 | 5/2001 | |
| WO | WO0182894 | 11/2001 | |

OTHER PUBLICATIONS

Post Presentation at AAPS, Nov. 1, 2000, W.R. Wilber et al., "Modified–Release Tablets Using Carbomer Resin in Direct Compression".
BFGoodrich Performance Materials, Carbopol® 71G marketing brochure, Oct. 2000.
H.A. Lieberman et al., editors, "Pharmaceutical Dosage Forms—Tablets", 1989, pp. 132–137, and 243–245 Marcel Dekker, Inc., New York.

* cited by examiner

Primary Examiner—Carlos Azpuru
Assistant Examiner—Micah-Paul Young
(74) Attorney, Agent, or Firm—Thoburn T. Dunlap; John E. Miller; Hudak, Shunk & Farine Co. LPA

(57) ABSTRACT

A directly-compressed, controlled release tablet contains N-acetyl cysteine as the active ingredient.

30 Claims, 1 Drawing Sheet

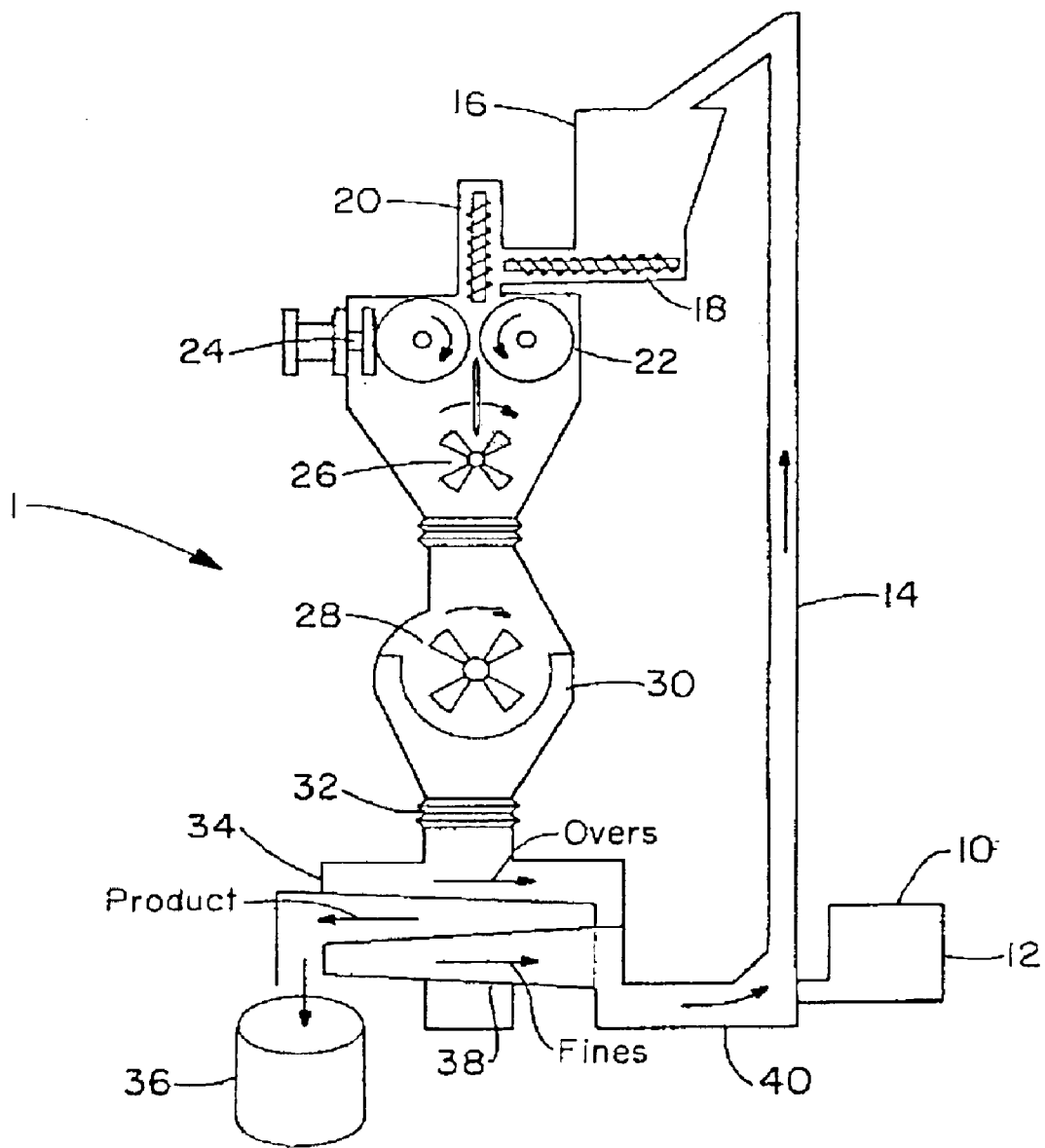

DOSAGE FORM OF N-ACETYL CYSTEINE

CROSS REFERENCE TO RELATED APPLICATIONS

The present application relates to commonly-assigned applications Ser. No. 09/329,471, filed Jun. 10, 1999, and Ser. No. 09/559,687, filed Apr. 27, 2000, the disclosures of which are incorporated herein by reference.

BACKGROUND OF INVENTION

Commonly-assigned application Ser. No. 09/329,471, filed Jun. 10, 1999, describes certain rheology modifying polymers derived from acrylic acid, methacrylic acid or analogues which exhibit enhanced controlled release properties when in granulated form. Commonly-assigned application Ser. No. 09/559,687, filed Apr. 27, 2000, teaches that these granulated rheology modifying polymers are particularly well suited for making solid dosage tablets and other articles by direct compression—i.e., by directly compressing a mixture of the tablet ingredients without granulating the mixture first.

SUMMARY OF INVENTION

It has now been found that the above technology is particularly well-suited for making tablets and other solid dosage pharmaceuticals in which N-acetyl cysteine is the active ingredient.

Thus, the present invention provides a directly-compressed, controlled release tablet or other article containing N-acetyl cysteine as the active ingredient. More particularly, the present invention provides a directly-compressed, controlled release tablet or other article containing about 25 to 80 wt. % N-acetyl cysteine, about 5 to 50 wt. % of a granulated, rheology modifying, release-controlling, slightly cross-linked polymer of acrylic acid, methacrylic acid or analogue, and optionally about 0 to 40 wt. % of an additional excipient, which preferably is a directly compressible binder.

In addition the present invention also provides new directly compressible compositions for making such tablets and articles as well as direct compression processes for forming tablets, caplets, and other solid dosage forms known to those skilled in the art.

BRIEF DESCRIPTION OF DRAWINGS

The FIGURE is a schematic of a compaction/granulation apparatus.

DETAILED DESCRIPTION

N-acetyl Cysteine

N-acetyl cysteine is a pharmaceutically active ingredient which dissolves or reduces the viscosity of mucous as produced in the respiratory airways, and including not only the lung tree but all the upper airways including the cavities in the forehead and the cheeks, to prevent or treat sinusitis, to thereby eliminate or reduce the symptoms of virus infections causing rhinitis, bronchitis and other respiratory tract congestion.

N-acetyl cysteine can also be used as a scavenger to prevent cell death due to free radicals, and to prevent nitrate intolerance following chronic treatment with nitroglycerine and sustained release nitrate formulations. N-acetyl cysteine also has value as a nutritional supplement. N-acetyl cysteine has few reported side effects except an irritating effect on the mucous membrane in the stomach. It also has an extremely bad taste which per se creates a great problem in administering it.

Another of the problems of N-acetyl cysteine is that it is readily hydrolyzed by a wide variety of enzymes, and is rapidly degraded and excreted from the body. Thus, to maintain a reasonable blood level requires frequent consumption of tablets.

N-Acetyl cysteine has hitherto been administered in the form of effervescent compositions which are dissolved in water by a carbon dioxide generating system prior to administration, or in the form of granules which are dissolved in water prior to use, or in the form of a matrix tablet comprising a skeleton of an insoluble polymer, which tablet leaks out N-acetyl cysteine into both the gastric and intestinal juices.

The problem with currently-available granulated and effervescent tablet compositions is that they release N-acetyl cysteine very rapidly. Thus, the effervescent compositions as well as the granulate compositions currently available on the market achieve a maximum blood plasma level within 1 hr from administration. One matrix tablet formulation does show a maximum blood plasma level at 2–2.5 hrs after administration, although its recipe indicates that granulation was required. The problem with granulation of acetyl cysteine is that if any dissolves, the dissolved material starts to decompose into impurities. One solution that has been tried is granulation in methylene chloride, which is a solvent of questionable toxicity and environmental effect.

In accordance with the present invention, this problem of overly-rapid release is obviated by providing the N-acetyl cysteine in the form of a tablet or other article made with the rheology modifying acrylic or methacrylic acid-based polymers, or analogues, described in commonly-assigned application Ser. No. 09/559,687, filed Apr. 27, 2000. Tablets made in this manner exhibit controlled release characteristics, thereby allowing the N-acetyl cysteine active ingredient to be released over a longer period of time.

N-acetyl cysteine is commercially available in a variety of different solid forms, varying in average particle size from less than 50 microns to over 600 microns, and all of these forms can be used in forming the tablets of the present invention. Indeed, solid N-acetyl cysteine having particle sizes such that 90 wt. % is between 25 and 1000 microns, preferably 50 to 750 microns, more preferably 100 to 500 microns, can be used to make tablets and pharmaceutical compositions in accordance with the present invention. Of course, the particle size of the N-acetyl cysteine will affect the rheology characteristics of the tableting mixture in which it is used. Accordingly, care must be taken, in particular applications of the present invention, to ensure that the particle size of the N-acetyl cysteine used is not too large or too small in light of the particular tableting equipment to be used. This can easily be determined by routine experimentation.

A particularly advantageous N-acetyl cysteine source is medium grade N-acetyl cysteine (#7302) available from the B. F. Goodrich Company, which has at least 90 wt. % of the particles with diameters between 100 and 500 microns, as measured by Air-Jet Sieve. As illustrated in the working examples below, directly compressible tablet-forming compositions made with this particular type of N-acetyl cysteine exhibit particularly good flow characteristics, which is important in connection with commercial manufacture of tablets in high speed tableting machines.

The amount of N-acetyl cysteine that can be included in the inventive tablet or other article can vary widely and essentially any amount can be used. Typically, the inventive tablet will contain about 25 to 80 wt. %, more typically about to 35 to 70 wt. % N-acetyl cysteine. Concentrations on the order of 50 to 60 wt. %, and especially about 54 wt. % are especially preferred.

Rheology Modifying Polymer

The rheology modifying polymers used in the present invention provide controlled release of the N-acetyl cysteine and other biologically active compounds contained in the inventive tablet, if any, so that when placed in water or body fluid, the polymer swells to form a viscous gel which retards diffusion of the active material. The rheology modifying polymers used in accordance with the present invention are the same rheology modifying polymers described in the above noted Ser. No. 09/559,687, filed Apr. 27, 2000 and comprise homopolymers or copolymers derived from one or more unsaturated carboxylic acid monomers generally having one or two carboxylic acid groups, desirably having one carbon to carbon double bond and containing generally a total of from 3 to about 10 carbon atoms and preferably from 3 to about 5 carbon atoms such as $\alpha$-$\beta$-unsaturated monocarboxylic acids, for example, acrylic acid, methacrylic acid, and crotonic acid, and the like, or dicarboxylic acids such as itaconic acid, fumaric acid, maleic acid, aconitic acid, and the like. Moreover, half ester monomers of such diacids with alkanols containing from 1 to about 4 carbon atoms can also be utilized. Preferred acids include acrylic acid or maleic acid.

Optionally, one or more oxygen containing unsaturated comonomers having a total of from 3 to about 40 carbon atoms, such as esters of the above unsaturated (di) carboxylic acids, that is mono or di, especially alkyl asters containing a total of from 1 to about 30 carbon atoms in the alkyl group can also be utilized as comonomers to form the rheology modifying polymers of the present invention. Examples of such esters include ethyl (meth)acrylate, butyl (meth)acrylate, 2-ethylhexyl (meth)acrylate, dodecyl (meth) acrylate, hexadecyl (meth)acrylate, and octadecyl (meth) acrylate, and the like, with the $C_{10}$ to $C_{30}$ (meth)acrylates being preferred.

Another optional class of comonomers are the various anhydrides of the above noted carboxylic acids such as maleic anhydride, and the like. Moreover, another optional class of suitable comonomers are the various alkyl vinyl ethers wherein the alkyl group contains from 1 to about 20 carbon atoms with examples including ethyl vinyl ether, methyl vinyl ether, and the like.

A further class of comonomers are monovalent ionic salts of polymerizable carboxylic acids or polymerizable polycarboxylic acids.

The amount of such comonomers that can be used to form the rheology modifying polymers of the present invention is generally a minor amount, such as from about 0.01% to about 40% by weight, desirably from about 0.5% to about 35% by weight, and preferably from about 1% to about 25% by weight based upon the total weight of monomers in the polymer. Thus, the amount of unsaturated carboxylic acid monomer, half ester thereof, or combinations thereof, is generally from about 60% to 99.99% by weight, desirably from about 65% to about 99.5% by weight, and preferably from about 75% to about 99% by weight based upon the total weight of monomers in the polymer.

The rheology modifying polymers of the present invention are generally anhydrous. That is, they generally contain 5 parts by weight or less, desirably 3 parts or 2 parts by weight or less, and preferably 1 part or less by weight, and even nil, that is no parts by weight, of water per 100 parts by weight of polymer.

The rheology modifying polymers also generally contain low amounts of multivalent metal cations such as iron, for example 1 part by weight or less, desirably 0.1 part by weight or less, and preferably 0.01 part by weight or less per 100 parts by weight of polymer. The rheology modifying polymers can contain up to five parts by weight of monovalent metal cations such as sodium, potassium, and the like.

An important aspect of the present invention is that the rheology modifying polymers are slightly cross-linked with one or more polyunsaturated monomers or comonomers. Suitable cross-linking agents generally include the various allyl ethers of sucrose or pentaerythritol, or derivatives thereof, or various polyalcohols. Specific examples include; diallylphthalate, divinyl benzene, allyl (meth)acrylate, ethylene glycol di(meth)acrylate, divinylglycol methylene bisacrylamide, trimethylolpropane tri (meth)acrylate, diallyl itaconate, diallyl fumarate, or diallyl maleate. Derivatives of castor oils or polyols such as esterfied with an ethylenically unsaturated carboxylic acid and the like can also be used. Preferred cross-linking agents include allyl ether of sucrose, allyl ether of pentaerythritol, diallylphthalate, and combinations thereof.

The amount of the cross-linking agent is from about 0.01 to about 2 parts by weight, desirably from about 0.02 to about 1.5 parts by weight, and preferably from about 0.03 to about 1 part by weight per 100 total parts by weight of monomers in the polymer. Slightly cross-linked rheology modifying polymers are utilized inasmuch as they can conform under light pressure as in a compacting apparatus and in a mill to form granular mixtures which readily flow. Highly cross-linked rheology modifying polymers tend to not conform under light pressure and consequently fracture in a mill thus forming fine sized particles which do not readily flow and are therefore unsuitable for forming a directly compressed solid dosage form. Such moderate to highly cross-linked polymers also tend to generate fisheyes therein. That is, when placed in-water, they exhibit incompletely swollen particles easily visible in the transparent gel. Uncrosslinked polymers will not gel properly.

Examples of commercially available, slightly cross-linked rheology modifying polymers which are suitable for use in the present invention include Carbopol®, 941, 971 PNF and 981 manufactured by B. F. Goodrich, as well as Synthalen L made by 3V/Sigma, Aqupec HV-501 and HV 501E made by Sumitomo Seika.

The rheology modifying polymers used in the present invention can be produced by conventional methods known to the art and to the literature such as by dispersion or precipitation polymerization utilizing suitable organic solvents such as various hydrocarbons, esters, halogenated hydrocarbon compounds and the like, with specific examples including aromatic solvents such as benzene, or toluene; various cycloaliphatic solvents such as cyclohexane; various esters such as ethyl acetate and methyl formate, ethyl formate; various chlorinated hydrocarbons such as dichloromethane; and combinations thereof. Preferred solvents generally include benzene, methylene chloride, blends of ethyl acetate and cyclohexane, or ethyl acetate, and the like.

The above monomers are polymerized in a manner known to the art and to the literature such as described in U.S. Pat. Nos. 2,798,053; 3,915,921; 4,267,103; 5,288,814; and 5,349,030 which are hereby fully incorporated by reference. Desirably, the rheology modifying polymers have an acidic pH in water, such as from about 2.0 to about 4.0, desirably from about 2.5 to about 3.5.

It is also an important aspect of the present invention to granulate the slightly cross-linked rheology modifying polymers. This can be accomplished by processes known to the art and to the literature such as for example by roller compaction, by slugging, or utilizing wet methods such as a fluidized bed.

A desired method for granulation is set forth in the drawing. A granulator, generally indicated by the numeral 1, contains a feeder 10 which feeds the slightly cross-linked rheology modifying polymer to the bottom of hopper 12. The polymer is then fed through feed channel 14 to upper hopper 16. Hopper 16 additionally contains oversized and/or fine sized granulated polymers which are not of a suitable size as set forth herein below. The slightly cross-linked polymer in hopper 16, along with the oversized and/or fine sized granulated polymers, is then fed via horizontal feed screw 18 to the granulator. The rate of rotation of horizontal feed screw 18 can be adjusted to permit continuous flow of the particulate mass of various sized polymer particles into the granulator without clogging. Then, vertical screw 20 compresses and deaerates the particulate mass and feeds the same into compaction rollers 22. Hydraulic actuator 24 applies a suitable pressure to the compaction rollers.

Pressure is applied to the compaction rollers via the hydraulic actuator or other compaction device to produce a compacted material having a density of about 0.3 g/cc to about 1.5 g/cc. Preferably, the density of the compacted material is from about 0.38 g/cc to about 0.5 g/cc. Compaction to these densities allows the aggregates and/or agglomerates which are subsequently formed from these polymers to exhibit the necessary crush strength. In addition, it also reduces the amount of undersized particles without removing so much of the voids, cracks and crevices (void volume) within these aggregates and agglomerates that uniform swelling in water or electrolyte solutions is prevented. The compaction rolls may have circumferential corrugations, pocket indentations or corrugations in the axial direction across the width of the roll.

Desirably, the compaction rollers rotate in opposite directions so that the various sized particles, flakes and chips of polymer fed thereto are pulled between the rollers, compressed, and subsequently dropped downwardly into pre-break mechanism 26. Pre-break mechanism 26 breaks the compressed various sized polymer chips into flakes which then fall into attritor 28. The attritor subsequently further breaks up the chips into flakes which fall through screen 30. The granulated particles then fall into screening apparatus 32 which generally contains a plurality of screens which separate out oversized as well as undersized (i.e. fines) particles. The desired sized particles are fed to product bin 36. The over and undersized particles 38 are recycled through feed mechanism 40 which directs the same into feed channel 14 thereby recycling the oversized and undersized particles to upper hopper 16. The above granulation procedure is set forth in U.S. patent application Ser. No. 09/329,471, filed Jun. 10, 1999 for Controlled Release Polyacrylic Acid Granules and a Process for Preparing the Same, the disclosure of which is hereby fully incorporated by reference.

The granulated rheology modifying polymers desirably have a specific particle size range so that when blended with N-acetyl cysteine and additional excipients, if any, a flowable mixture is produced. Desirably, the particle or granular size of the polymer can be classified as falling within size ranges as defined by U.S. Standard Mesh screens. For example, the particle size of the granulated polymers especially useful in accordance with the present invention is that which generally falls through 40 mesh but is retained on 200 mesh, desirably that which falls through 45 mesh but is retained on 150 mesh, and preferably that which falls through 50 mesh but is retained upon a 100 mesh screen.

As appreciated by those skilled in the art, pharmaceutical compositions which are classified by particle size often contain some oversized and/or some undersized material. For example, oversized material may be contained within a desired particle size range as when the particles are elongated. Undersized particles, or fines, can also be found within the desired particle size ranges when the same stick to or are tied up between desired particle size products. However, the amount of oversized or undersized material is also generally limited. Thus, the amount of the oversized material contained in the granulated rheology modifying polymers of the present invention, when classified to within the above desired ranges, is generally about 5 percent or less, desirably about 3 percent or less, and preferably about 1 percent or less by weight. Similarly, the amount of fines in these granulated polymers when classified to within the above desired ranges is generally about 25 percent or less, desirably about 20 percent or less, and preferably about 15 percent by weight or less. The net result is that rheology modifying polymers of the present invention, when classified as described above, take the form of free flowing particulate masses which not only can be directly compressed but which are also capable of easily flowing through dies and other constrictions without clogging.

Note that the same cannot be said for otherwise identical polymers which are moderate to highly cross-linked. That is to say, polymers which are similarly granulated and classified and of essentially the same chemical composition, except for being moderately to highly cross-linked, will not form such free-flowing particulate masses as they tend to fracture and form excessive amounts of fines which clog when passed through narrow diameter dies or other constrictions. Moreover, if compressed to avoid formation of excessive amounts of fines, these other polymers tend to form fisheyes as described above, and swelling is impeded so that desirable control release properties are not achieved.

The granulated slightly cross-linked rheology modifying polymers of the present invention have several favorable properties such as thickening efficiency, bulk density, and tap density. When dispersed in water at a concentration of 10 grams per liter and neutralized to a pH of 7, the granulated polymers generally retain at least 70, 80, and even 90 percent of the thickening capacity of the original powder. The viscosity of such a solution is desirably at least 350, 400, or 450, and preferably at least 1,400, 1,600, or 1,800 centipoise to about 16,000 centipoise.

The bulk density of the granules is measured according to a typical bulk density method for powders. A 30–100 mL cup is used which can be lightly tapped one time after filling. The powder is dropped from a powder funnel which discharges about 4.6–8 cm above the rim of the cup. The excess material which accumulates above the rim of the cup can be removed by scraping with a spatula and the weight of the contents determined. The bulk density is the weight of the contents divided by their volume. Suitable bulk densities generally range from about 0.35 to about 0.60 and desirably from about 0.38 to about 0.55 grams per cubic centimeter. A tap density can also be determined using a 100 mL graduated cylinder instead of a cup. The powder is discharged from the bottom of a powder funnel as set forth above. A tap density apparatus such as a J. Engelsmann AG Tap Density Apparatus is used to tap the cylinder and contents 1,000 times. The volume and weight of the powder after tapping is recorded and the density is calculated as the weight divided by the volume. Suitable tap densities range from about 0.40 to about 0.70, desirably from about 0.42 to about 0.60 and preferably from about 0.45 to about 0.58 grams per cubic centimeter.

A particularly attractive rheology modifying polymer for use in the present invention comprises a polyacrylic acid polymer, lightly crosslinked with allyl ethers of pentaerythrytol, prepared by precipitation polymerization, dried, and further processed as described in application Ser. No. 09/329,471, filed Jun. 10, 1999, and processed to a particle size distribution where greater than 60 wt. % lies between 180 microns and 425 microns, and greater than 85 wt. % lies between 75 and 425 microns, as measured by Air-Jet Sieve. Furthermore, this material has a Flo-Dex® index of 16 mm or less, preferably 12 mm or less.

The amount of rheology modifying polymer that can be included in the inventive tablet can vary widely and essentially any amount can be used. Typically, the inventive tablet will contain 5 to 50 wt. %, more typically 10 to 40 wt. %, or even 15 to 35 wt. % rheology modifying polymer. Concentrations on the order of 20 to 30 wt. %, and especially about 25 wt. % are especially preferred.

Additional Excipients

In addition to the rheology modifying polymers described above, the inventive tablets also may contain additional excipients. As used herein, excipient means a substance added to a tablet-forming formulation which is not pharmaceutically active. Additional excipients can be used in accordance with the present invention for the purpose of forming the tablet into proper shape, holding the components of the tablet together, facilitating production or manufacture of the tablet (i.e., facilitating use of an automated tablet press), facilitating dissolution of the tablet after it has been administered, as well as other properties advantageous for making and using tablets and other solid dosage articles. Excipients may also be utilized to give a desirable slow release profile as well as other desirable attributes of a compressed tablet such as color, hardness, crushing strength, and low friability, etc. Accordingly, such excipients can be one or more fillers, binders, colorants, coating agents, slow release compounds, lubricants, glidants, antiadherents, and the like.

As appreciated by those skilled in the art, excipients can be broadly classified as directly compressible excipients and non-directly compressible excipients. In this context, a directly-compressible excipient is one which if used as the sole excipient would allow the formulation to flow well enough to run on an automated high speed tablet machine without granulation of the formulation. However, in addition to flowability, tableting formulations need to have enough compressibility to compact under pressure into a cohesive mass having sufficient crush strength (i.e., at least 7 kilopounds), resistance to abrasion and spontaneous physical disintegration or capping. Many non-directly compressible binders added to promote physical robustness would, if used as the sole excipient, impart insufficient flow to the formulation without granulation of the formulation first. Thus, when non-directly compressible binders or other excipients are used, a balance between the directly compressible excipients and non-directly compressible excipients should be determined, as is familiar to those skilled in the art, to provide an overall formulation which can flow well enough to be directly compressible itself without granulation, but which also has the property of compressibility into a robust solid dosage form.

Examples of suitable directly compressible excipients exhibiting binder functions include microcrystalline cellulose such as Avicel® PH101, Avicel® PH102, Avicel® PH200, Avicel® PH301, and Avicel® PH302 available from FMC Corporation; Vivapur 101 and Virapur 102 available from Rettenmaier and Sohne GMBH; Emcocel 50 M and Emcocel 90 M available from Penwest Company; dicalcium phosphate such as Elcema® available from Degussa; A-Tab® and DiTab® available from Rhodia; lactose monohydrate such as Flow-Lac® 100, Pharmatose® DCL11, Pharmatose DCL15, Pharmatose® DCL21 available from DMV International; Tablettose® 80 available from Meggle; and tricalcium phosphate such as Tri-Tab® FastFlo® Lactose from Foremost; and Prosolve® (silicified MCC) from Penwest.

A binder excipient that is particularly advantageous in accordance with the present invention is Avicel® PH101, which is a microcrystalline cellulose having the ability to flow in direct compression, but also to deform in a plastic manner during compression in the die. Avicel® PH101 is also well-known to improve friability of tablets.

The amount of additional excipient that can be included in the inventive tablet can vary widely and essentially any amount can be used. For example, amounts of 0 to 50 wt. % or more, based on the total weight of ingredients in the tablet can be used. More typically, an additional excipient will be present in an amount about 5 to 40 wt. %, more preferably 10 to 30 wt. %, or even 15 to 25% wt. %, with additional excipient amounts of about 20 to 21 wt. % being especially preferred, particularly if these additional excipients exhibit a binder function.

Lubricants

It is also desirable to include a lubricant in the inventive tablet or other solid dosage article. Lubricants are excipients which serve to facilitate movement of the tablet-forming formulation through an automated tablet press without causing malfunction of the machine. Examples of suitable lubricants are magnesium stearate, zinc stearate, and stearic acid. Magnesium stearate is preferred.

The amount of lubricant that can be included in the inventive tablet can vary widely and any conventional amount can be used. Typical lubricant concentrations are 0.2 to 2 wt. %, preferably 0.3 to 1 wt. %, more preferably about 0.5 wt. %.

Additional Pharmaceutically Acting Ingredients

In additional to N-acetyl cysteine, the tablet of the present invention can also include other pharmaceutically active ingredients such as decongestants, stimulants, vitamins, minerals, nutraceuticals, and nutritional supplements as well as the other pharmaceutically active ingredients identified in the above noted application Ser. No. 09/559,687, filed Apr. 27, 2000.

Tablet Formation

The present invention is especially suitable for use in making tablets. In this connection, tablet as used herein means any solid dosage article regardless of size or shape which is capable of being ingested by the patient (human or animal) being treated and which is formed by compaction or agglomeration. Normally, the invention will be used in forming conventional tablets, pills and caplets—i.e., small, rounded, compact masses of various different shapes which are small enough to be swallowed easily yet large enough to be easily handled. The invention, however, can be used to make other solid dosage articles such as suppositories and implants, for example.

The inventive tablets are made by first mixing the ingredients thereof in any conventional manner to produce a blend. For example, the ingredients can be mixed in a shell blender, a Vee blender, a double-cone blender, a ribbon mixer, and the like.

The mixture is then directly fed into a tablet making machine wherein a desired amount of the mixture or blend is fed through an orifice or opening into a tablet die. The die is closed and compresses the mixture to produce a suitable sized and shaped tablet. Unexpectedly, the ingredient mixture can be directly fed into the tablet forming machine without granulating the entire mixture first, which is generally necessary if ungranulated rheology modifying polymers or non-directly compressible excipients are used. That is, tablets and other solid dosage articles of acceptable structural integrity can be made in accordance with the present invention without any other processing or compounding steps between formation of the ingredient mixture and compaction of the mixture into a tablet or other solid dosage article. This is because they are formed from the above rheology modifying polymer and other optional direct compression excipients rather than other excipients and ingredients conventionally used in tablet formation.

The tableting mixtures made in accordance with the present invention have suitable flow properties or flow indices which can be readily determined in a manner known to the art and to the literature. For example, the flow index can be measured by Flodex™ equipment, which comprises a 35–45 mm diameter tube approximately 8–10 cm long. Bottom caps with incrementally larger diameter apertures are used in the apparatus until the aperture is found of sufficient diameter that the contents of the tube are substantially emptied from the tube when the aperture is unblocked by the operator. A flow index value is assigned equal to the diameter of the aperture in mm through which the material flows easily. If the aperture is too small, then bridging over occurs with a substantial amount of the tube contents being retained in the tube. The tableting mixtures of the present invention have Flodex™ values of generally 25 or 20 or less, desirably 15 or 10 or less, and preferably 8, 6, 5, or 4 or less, and even 3 or less.

The required Flodex™ index values are directly related to the diameter of the die tooling of the tablet press. Desirably, the flow characteristics of the compressible mixture of the present invention is such that it can flow through a hole of the same size or smaller than the die diameter in which the tablet is to be made. In other words, if the tablet diameter is 16 mm, the compressible mixture should at least be able to flow through a 16 mm hole, desirably a hole of diameter of 1 mm smaller, i.e. 15 mm, and preferably a diameter of at least 2 mm less, i.e. 14 mm or smaller.

The present invention provides a simple formulation of N-acetyl cysteine which has excellent flowability (Flodex™ index as low as 5 mm), and which can be directly compressed into robust tablets (friability 0.04%; disintegration time 1 hour). As a result, separate granulation of the entire ingredient mixture, which would be necessary if other rheology modifying polymers and excipients were used in a similar dry compaction process, is avoided. In addition, the use of organic solvents, which would be necessary if wet granulation techniques were used to form compressible granules to form these tablets owing to the solubility of N-acetyl cysteine in water, is also avoided.

EXAMPLES

The invention may be better understood by reference to the following examples, which serve to illustrate but not to limit the present invention.

Example 1

A formulation having the composition shown in Table 1 below (except for the magnesium stearate) was blended in a Vee-blender for 20 minutes Composition of Formulation of Example 1

| Ingredients (to be well mixed) | Concentration, wt % |
|---|---|
| Polyacrylic acid polymer (slightly crosslinked with allyl ethers of pentaerythrytol) where 85 wt. % of particles are between 75 and 425 microns and where Flodex ™ index is 12 mm or less (Carbopol ® 71 G, B. F. Goodrich) | 25.0 |
| N-Acetylcysteine where 90 wt. % of particles are between 100 and 500 microns (medium grade, #7302 B. F. Goodrich Company) | 54.0 |
| Microcrystalline Cellulose Avicel ® PH101 (available from FMC Corporation) | 21.0 |
| Intermediate Total | 100.0 |
| Magnesium Stearate (Lubricant) | 0.5 |
| Total | 100.5 |

Next, 0.5 wt. % magnesium stearate, based on the weight of the other ingredients, was added and the mixture was further blended for an additional three minutes.

The properties of the mixture were then measured, including Flodex™ flowability, as described above. The powder was filled into the test cylinder to a specific height, clearing the bottom orifice, while flow of the powder through the orifice was observed. The Flodex™ number is the smallest diameter orifice (in mm) through which the powder flowed freely. In addition, powder flow rate in g/sec through a 10 mm diameter funnel was also measured.

Bulk density of the mixture was also measured using a 30–100 mL cup which was lightly tapped one time after filling. The powder was dropped from a powder funnel which discharged about 4 to 8 cm above the rim of the cup. The excess material which accumulated above the rim of the cup was removed by scraping with a spatula and the weight of the contents was determined. The bulk density was the weight of the contents divided by their volume.

Tap density was also determined using a 100 mL graduated cylinder instead of a cup. The powder was discharged from the bottom of a powder funnel. A J. Engelsmann AG Tap Density Apparatus was used to tap the cylinder and contents 1,000 times. The volume and weight of the powder after tapping was recorded and the density was calculated as the weight divided by the volume.

Hausner ratio is tap density divided by bulk density. Values for the Hausner ratio which are near 1.0 indicate that the mixture will not compress well in the die. Hausner ratio values that are near 2.0 indicate that the mixture will undergo extreme compression in the die with concomitant long distances of punch travel during compression and increased wear of the punches and dies.

Compressibility index is equal to one minus the ratio of bulk density to tap density (1—(bulk density/tap density)) and is expressed as a percent. Compressibility index is related to the Hausner ratio and is also used by those skilled in the art to estimate performance in the die. Compressibility index values near 0% (Hausner index of 1.0) indicate that the powder mixture will not deform and compress into a cohesive mass in the die. Compressibility index values near 50% (Hausner index of 2.0) indicate long distances of punch travel, as above. A compressibility index in the range of 18% to 25% is predictive of a well-behaved formulation.

As can be seen from Table 2 below, the mixture had a Flodex™ index of 5 mm., indicating that it would flow into an orifice having a diameter of 5 mm or larger, a flow rate of 5.1 g/sec. through a 10 mm. diameter funnel, indicating that it would flow freely through a pipe or hopper of that diameter or larger, a bulk density of 0.53 and a tap density of 0.683. The Hausner ratio of 1.289 predicts a well-performing formulation, as does the compressibility index of 22.1%.

Physical Properties of Ingredient Mixture

| Property | Measured Value |
| --- | --- |
| Flodex ™ Index (mm) | 5 |
| Flow Rate (g/sec) | 5.1 |
| Bulk Density (g/cc) | 0.530 |
| Tap Density (g/cc) | 0.683 |
| Hausner Ratio | 1.289 |
| Compressibility Index (%) | 22.40 |

The granular mixture was then hand-tableted using a single-punch Stokes press (0.375 inch diameter concave dies). Initially, several tablets were struck off at the highest compression force achievable by the machine, in order to determine the maximum hardness achievable from this formulation. The maximum attainable hardness of the formulation was determined to be 14 Kp.

Although the USP recommends hardness of 7 to 12 Kp for 300 mg tablets, the tablet size used here, it was important to determine maximum attainable hardness of the formulation. Very often, when an automated press is operating at high speed, the dwell time of the punches against the tablet is not long enough to ensure relaxation into a robust mass by plastic deformation. Under these conditions, the rapid shock of the compression may be recovered by elastic recovery processes, and the compression pressure may need to be set even higher in order to achieve the desired target hardness. Thus, it was important to pre-test to determine what latitude existed for increasing hardness. The more latitude that exists, the more likely it is that robust tablets can be obtained at high speed. Here, the 14 Kp hardness of the formulation indicates that robust tablets can be obtained at high speed.

After the maximum attainable hardness had been determined, the compression force was backed off until tablets having the target hardness (7 to 12 Kp) were produced, and the formulation was run out. The hardness of the tablets so obtained was measured at 8.5 Kp (see Table 3), using a Schleuniger 2E® hardness tester, indicating the tablets met the targeted hardness over the entire run.

In addition, friability (USP 23 NF 18), which is a measure of the ease of breaking or pulverizing the tablets, was measured using a Vanderkamp® friability tester. The friability of 0.04% (see Table 3), indicates that the tablets had extremely good compaction, robustness, and physical integrity. The USP allows up to 1% loss in the friability test.

Disintegration times in deionized water were also measured using an Erweka Disintegration Tester Model ZT62®. The disintegration time of 1:19:16 (see Table 3), indicates that the tablet has a long resistance to physical degradation on contact with water.

The results obtained are set forth in Table 3 below.

Physical Properties of Tablets

| Property | Value | Standard Deviation |
| --- | --- | --- |
| Tablet Weight (mg) | 301 | 2.1 |
| Hardness (Kp) | 8.5 | 0.55 |
| Friability (%) | 0.04 | — |
| Disintegration (h:m:s) | 1:19:16 | 0:13:36 |

Finally, the tablets obtained in this way were tested for release time by USP Dissolution Apparatus II (Paddle Type) using a dissolution medium of Simulated Gastric Fluid at a temperature of 37 degrees Centigrade as described in the USP. The drug concentration in the dissolution bath was monitored by HPLC. The results of this test showed that tablets exhibited an average release time for the N-acetylcysteine active ingredient of approximately 80 minutes.

Therefore, as can be seen from this example, the ingredient mixture described above was directly compressed into tablets having excellent structural integrity without any intervening or intermediate processing step being carried out on the tablet-forming mixture. Rather, tablet formation was easily accomplished simply by flowing a suitable amount of the mixture into the tableting die and compressing the same. The process is thus free of any other steps.

It will therefore be appreciated that N-acetylcysteine tablets exhibiting excellent structural integrity and excellent slow release properties can be made in accordance with the invention by dry compression techniques even though the ingredient mixture used for tablet formation is not further processed for affecting its rheology, or its ability to agglomerate by compaction, prior to the tablet forming step.

Example 2

Example 1 was repeated, except that fine grade N-acetyl cysteine (#7027, available from B. F. Goodrich Company) was used in place of the medium grade N-acetyl cysteine used in Example 1. Whereas the medium grade of N-acetyl cysteine has greater than 90 wt. % of particles between 100 and 500 microns in size, the fine grade has greater than 50 wt. % smaller than 100 microns.

The ingredient mixtures so obtained exhibited a Flodex™ index of 18 mm, rather than 5 as in the case of Example 1. More importantly, its flow rate through a 10 mm diameter funnel was 0.0 g/sec as compared to 5.1 g/sec. This formulation would not work well on a tablet press having die tooling of 0.375 inch (9.5 mm), but the Flodex™ result implies that it would work on a tablet press having 18 mm tooling.

These data indicate that the morphology and particle size of the active ingredient can determine whether the formulation will flow and run on a high-speed tablet press of a particular tooling size. Similarly, the identity, morphology, particle size and particle size distributions of the other ingredients, and the formulation as a whole, are critical to its performance in tableting and in the final tablets.

Although only a few embodiments of the present invention have been described above, it should be appreciated that many modifications can be made without departing from the spirit and scope of the invention. All such modifications are intended to be included within the scope of the present invention, which is to be limited only by the following claims.

What is claimed is:

1. A composition capable of being directly compressed in a high speed tableting machine producing controlled release tablets said composition comprising
   (a) 25 to 80 wt. % of N-acetyl cysteine having average particle size between 50 and 600 microns such that 90 wt. % is between 25 and 1000 microns;
   (b) 10 to 40 wt. % of a rheology modifying polymer derived from (i) at least one unsaturated carboxylic acid or dicarboxylic acid monomer having a total of 3 to about 10 carbon atoms, or at leat one half ester of these unsaturated dicarboxylic acid monomers with an alkanol having from 1 to about 4 carbon atoms, or combinations thereof, (ii) optionally one or more oxygen containing unsaturated comonomers having from 3 to about 40 carbon atoms, and (iii) 0.01 to 2 parts by wt. per 100 parts by weight of monomers of a cross-linking agent, said polymer having particles sized from about 40 mesh to about 200 mesh provided that said particles have 5 percent or less of oversized particles and 25 percent or less of undersized particles; the bulk density of said polymer particles is from about 0.35 to about 0.60 g/cc and tap density is from about 0.40 to about 0.70 g/cc.

2. A tablet obtained by directly compressing a composition on a high speed tableting machine, said composition comprising
   (a) 25 to 80 wt. % of N-acetyl cysteine having average particle size between 50 and 600 microns such that 90 wt. % is between 25 and 1000 microns;
   (b) 10 to 40 wt. % of a rheology modifying polymer derived from (i) at least one unsaturated carboxylic acid or dicarboxylic acid monomer having a total of from 3 to about 10 carbon atoms, or at least one half ester of these unsaturated dicarboxylic acid monomers with an alkanol having from 1 to about 4 carbon atoms, or combinations thereof, (ii) optionally one or more oxygen containing unsaturated comonomers having from 3 to about 40 carbon atoms, and (iii) 0.01 to 2 parts by weight per 100 parts by weight of monomers of a cross-linking agent, said polymer having particles sized from about 40 mesh to about 200 mesh provided that said particles have 5 percent or less of oversized particles and 25 percent or less of undersized particles; the bulk density of said polymer particles is from about 0.35 to about 0.60 g/cc and tape density is from about 0.40 to about 0.70 g/cc.

3. The composition of claim 1 wherein the composition contains a directly compressible excipient.

4. The composition of claim 1 wherein the rheology modifying polymer includes at least one oxygen containing unsaturated comonomer having a total of 3 to about 40 carbon atoms and being selected from the group consisting of
   (i) esters formed from unsaturated carboxylic acid or dicarboxylic acids having a total of from 3 to about 10 carbon atoms and alkyl groups having 1 to 30 carbon atoms,
   (ii) anhydrides of unsaturated dicarboxylic acids having a total of from 3 to about 10 carbon atoms, and
   (iii) alkyl vinyl ethers in which the alkyl group contains 1 to about 20 carbon atoms.

5. The composition of claim 4, wherein the cross-linking agent is an allyl ether of sucrose or pentaerythritol, or a derivative thereof, a polyalcohol, diallylphthalate, divinyl benzene, allyl acrylate or methacrylate, ethylene glycol diacrylate or dimethacrylate, methylene bisacrylamide, trimethylolpropane triacrylate or trimethacrylate, diallyl itaconate, diallyl fumarate, diallyl maleate, castor oil or a polyol esterified with an ethylenically unsaturated carboxylic acid, or combinations thereof.

6. The composition of claim 1, wherein the rheology modifying polymer contains
   (a) about 60 to 90 percent by weight of unsaturated carboxylic acid or dicarboxylic acid monomer having a total of from 3 to about 10 carbon atoms, or at least one half ester of these unsaturated dicarboxylic acid monomers with an alkanol having from 1 to about 4 carbon atoms, or combinations thereof, and
   (b) about 0.01 to 40 percent by weight of an unsaturated comonomer having from 3 to about 40 carbon atoms.

7. The composition of claim 1, wherein the rheology modifying polymer is derived from acrylic acid or maleic acid, or combinations thereof, wherein said cross-linking agent is an allyl ether of sucrose, an allyl ether of pentaerythritol, or diallyphthalate, or combinations thereof, and wherein the amount of cross-linking agent in the polymer is from about 0.03 to about 1.0 part by weight per 100 parts by weight of monomers (a) and comonomes (b).

8. The composition of claim 7, wherein said composition includes a binder.

9. The composition of claim 8, wherein the binder is microcrystalline cellulose.

10. The composition of claim 8, wherein the composition contains
    about 50 to 60 wt. % N-acetyl cysteine,
    about 20 to 30 wt. % of the rheology modifying polymer, and
    about 15 to 25 wt. % binder.

11. The composition of claim 8, wherein at least about 90 wt. % of the N-acetyl cysteine has a particle size between 100 to 500 microns.

12. The composition of claim 11, wherein the composition contains about 0.2 to 2 wt. % of a lubricant.

13. The composition of claim 12, wherein the composition contains
    about 54 wt. % medium grade N-acetyl cysteine,
    about 25 wt. % of the rheology modifying polymer,
    about 20 to 21 wt. % binder, and
    about 0.5 wt. % magnesium stearate.

14. The composition of claim 1, wherein the rheology modifying polymer contains less than about 2 parts by weight of water and less than about 1 part by weight multivalent metal cation per 100 parts by weight polymer.

15. The composition of claim 1, wherein the rheology modifying polymer contains less than about 5 parts by weight of water and less than about 0.1 part by weight multivalent metal cation per 100 parts by weight polymer.

16. The composition of claim 3, wherein said excipient comprises one or more of fillers, binders, colorants, coating agents, disintegrants, lubricants, glidants, antiadherents or slow release compounds.

17. A tablet obtained by directly compressing a composition of claim 3 on a high speed tableting machine.

18. A tablet obtained by directly compressing a composition of claim 4 on a high speed tableting machine.

19. A tablet obtained by directly compressing a composition of claim 5 on a high speed tableting machine.

20. A tablet obtained by directly compressing a composition of claim 6 on a high speed tableting machine.

21. A tablet obtained by directly compressing a composition of claim 7 on a high speed tableting machine.

22. A tablet obtained by directly compressing a composition of claim 8 on a high speed tableting machine.

23. A tablet obtained by directly compressing a composition of claim 9 on a high speed tableting machine.

24. A tablet obtained by directly compressing a composition of claim 10 on a high speed tableting machine.

25. A tablet obtained by directly compressing a composition of claim 11 on a high speed tableting machine.

26. A tablet obtained by directly compressing a composition of claim 12 on a high speed tableting machine.

27. A tablet obtained by directly compressing a composition of claim 13 on a high speed tableting machine.

28. A tablet obtained by directly compressing a composition of claim 14 on a high speed tableting machine.

29. A tablet obtained by directly compressing a composition of claim 15 on a high speed tableting machine.

30. A tablet obtained by directly compressing a composition of claim 16 on a high speed tableting machine.

* * * * *